(12) United States Patent
Hoff et al.

(10) Patent No.: US 11,517,622 B2
(45) Date of Patent: *Dec. 6, 2022

(54) COMBINATION OF REGORAFENIB AND PD-1/PD-L1(2) INHIBITORS FOR TREATING CANCER

(71) Applicant: BAYER AKTIENGESELLSCHAFT, Leverkusen (DE)

(72) Inventors: Sabine Hoff, Potsdam (DE); Lars Rose, Berlin (DE); Dieter Zopf, Berlin (DE); Fabian Kiessling, Aachen (DE); Wiltrud Lederle, Aachen (DE); Dennis Doleschel, Aachen (DE)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/731,412

(22) Filed: Dec. 31, 2019

(65) Prior Publication Data

US 2020/0188372 A1 Jun. 18, 2020

Related U.S. Application Data

(63) Continuation of application No. 16/617,642, filed as application No. PCT/EP2018/063785 on May 25, 2018.

(30) Foreign Application Priority Data

Jun. 2, 2017 (EP) .................................... 17174169

(51) Int. Cl.
| | | |
|---|---|---|
| *A61K 39/395* | (2006.01) | |
| *A61P 35/00* | (2006.01) | |
| *A61K 9/00* | (2006.01) | |
| *A61K 31/44* | (2006.01) | |
| *A61K 39/00* | (2006.01) | |

(52) U.S. Cl.
CPC ........ *A61K 39/3955* (2013.01); *A61K 9/0019* (2013.01); *A61K 31/44* (2013.01); *A61P 35/00* (2018.01); *A61K 2039/505* (2013.01)

(58) Field of Classification Search
CPC ............ A61K 39/3995; A61K 2300/00; A61K 31/44; A61K 39/3955; A61K 45/06; A61K 2039/505
See application file for complete search history.

(56) References Cited

U.S. PATENT DOCUMENTS

| | | | |
|---|---|---|---|
| 8,637,553 | B2 | 1/2014 | Boyer et al. |
| 9,458,107 | B2 | 10/2016 | Stiehl et al. |
| 9,957,232 | B2 | 5/2018 | Grunenberg et al. |
| 10,570,202 | B2 | 2/2020 | Martini et al. |
| 10,869,926 | B2 | 12/2020 | Zhou et al. |
| 2014/0065212 | A1 | 3/2014 | Skrabs et al. |
| 2015/0202214 | A1 | 7/2015 | Weber et al. |
| 2017/0112925 | A1 | 4/2017 | Junttila |
| 2017/0165364 | A1 | 6/2017 | Ito et al. |
| 2017/0189526 | A1 | 7/2017 | Zhou et al. |
| 2017/0209574 | A1 | 7/2017 | Cao et al. |
| 2017/0313775 | A1 | 11/2017 | Diaz et al. |
| 2017/0354657 | A1 | 12/2017 | Bekker et al. |
| 2019/0022092 | A1 | 1/2019 | Rothbaum et al. |
| 2019/0125867 | A1 | 5/2019 | Ito et al. |
| 2019/0183972 | A1 | 6/2019 | Gaynor |
| 2021/0052729 | A1 | 2/2021 | Zhou et al. |

FOREIGN PATENT DOCUMENTS

| | | | | |
|---|---|---|---|---|
| JP | 2015527395 | A | 9/2015 | |
| WO | 05009961 | A2 | 2/2005 | |
| WO | 2007/054303 | A2 | 5/2007 | |
| WO | 08043446 | A1 | 4/2008 | |
| WO | 11128261 | A1 | 10/2011 | |
| WO | 14048881 | A1 | 4/2014 | |
| WO | 15119930 | A1 | 8/2015 | |
| WO | 15125652 | A1 | 8/2015 | |
| WO | 16010879 | A1 | 1/2016 | |
| WO | 16011160 | A1 | 1/2016 | |
| WO | WO-2016054555 | A2 * | 4/2016 | ........... A61K 9/0053 |
| WO | 16173959 | A1 | 11/2016 | |
| WO | WO-2017046746 | A1 * | 3/2017 | ........... A61K 31/454 |

OTHER PUBLICATIONS

Pardoll (Nature Reviews Cancer, 2012, vol. 12, pp. 252-264) (Year: 2012).*
Tsai et al (Cancer Immunology Research, 2017, vol. 5, pp. 790-803) (Year: 2017).*
Yoshino et al (Investigational New Drugs, 2015, vol. 33, pp. 740-750) (Year: 2015).*
The abstract of Overman (Journal of Clinical Oncology, Feb. 1, 2017, vol. 35, No. 4, suppl., p. 519) (Year: 2017).*
Gharwan and Groninger (Nature Reviews Clinical Oncology, 2016, vol. 13, pp. 209-227) (Year: 2016).*
Topalian et al, Cancer Cell, 2015, vol. 27, pp. 450-461 (Year: 2015).*
Schietinger et al (Immunity, 2016, vol. 45, pp. 389-401) (Year: 2016).*
Liu et al (Journal of Immunotherapy, 2016, vol. 39, pp. 171-180) (Year: 2016).*
Zopf et al (Cancer Medicine, 2016, vol. 5, pp. 3176-3185) (Year: 2016).*
Tang et al (Cellular Physiology and Biochemistry, 2013, vol. 32, pp. 827-837) (Year: 2013).*
Iwai et al (Journal of Biomedical Science, Apr. 4, 2017, vol. 24:26, 11 pages) (Year: 2017).*

(Continued)

*Primary Examiner* — Karen A. Canella

(74) *Attorney, Agent, or Firm* — Millen White Zelano and Branigan, PC; Richard J. Traverso

(57) ABSTRACT

The present invention relates to pharmaceutical compositions and combinations comprising regorafenib or its hydrate, solvate, metabolite or pharmaceutically acceptable salt or a polymorph thereof and a PD-1/PD-L1(2) inhibitor for treating, preventing or managing diseases and conditions including hyperproliferative disorders such as cancer in humans and other mammals.

24 Claims, 1 Drawing Sheet

(56) References Cited

OTHER PUBLICATIONS

Lowe et al (Advances in Protein Chemistry and Structural Biology, 2011, vol. 84, pp. 41-61) (Year: 2011).*
Park Junsik et al: "Immune checkpoint inhibitors for cancer treatment", Archives of Pharmacal Research, Natl. Fisheries University, Pusan, KR, vol. 39, No. 11, Oct. 21, 2016 (Oct. 21, 2016), pp. 1577-1587, XP036106757, ISSN: 0253-6269, [retrieved on Oct. 21, 2016], DOI: 10.1007/S12272-016-0850-5.
Masatoshi Kudo: "Recent Trends in the Management of Hepatocellular Carcinoma with Special Emphasis on Treatment with Regorafenib and Immune Checkpoint Inhibitors", Digestive Diseases: Clinical Reviews, vol. 34, No. 6, Oct. 18, 2016 (Oct. 18, 2016), CH, pp. 714-730, XP055488316, ISSN: 0257-2753, DOI: 10.1159/000448864.
International Search Report PCT/W02018/063785 dated Jul. 18, 2018 (pp. 1-3).
Obuch et al, Colorectal cancer genetics is changing everything; Gastroenterology Clinics of North America, 45:459-476, 2016.
Graham et al, Molecular Subtypes and Personalized Therapy in Metastatic Colorectal Cancer; Curr Colorectal Cancer Rep, 12;141-150, 2016.
Abou-Elkacem L. et al, Regorafenib inhibits growth, angiogenesis, and metastasis in a highly aggressive, orthotopic colon cancer model; Mol Cancer Ther, 2013,12(7),1322-1331.
Bersanelle et al., From targeting the tumor to targeting the immune system: Transversal challenges in oncology with the inhibition of the PD-1/PD-L1 axis; World Journal of Clinical Oncology, 2017, 8(1), 37-53.
Ettrich and Seufferlein ('Regorafenib', In Small Molecules in Oncology, Recent Results in Cancer Research, 2014, vol. 201, pp. 185-196, Martins, Ed.) (Year: 2014).
International Search Report PCT/W02018/063785 dated Jul. 18, 2018 (pp. 1-17).
PCT Request for PCT/EP2018/063785 dated May 25, 2018 (BHC171043_WoRequest) pp. 1-5.
Bruix J. et al., Regorafenib for patients with hepatocellular carcinoma who progressed on sorafenib treatment (RESORCE): a randomised, double-blind, placebo-controlled, phase 3 trial; Lancet, 2017, vol. 389 (10064), 56-66.
Demetri G.D. et al., Efficacy and safety of regorafenib for advanced gastrointestinal stromal tumours after failure of imatinib and sunitinib (GRID): an international, multicentre, randomised, placebo-controlled, phase 3 trial; Lancet, 2013, vol. 381 (9863), 295-302.
Ettrich et al: "Regorafenib"; Small Molecules in Oncology, Recent Results in Cancer Research 201, (2014) pp. 185-196.
Grothey A. et al., Regorafenib monotherapy for previously treated metastatic colorectal cancer (CORRECT): an international, multicentre, randomised, placebo-controlled, phase 3 trial; Lancet, 2013, 381 (9863) 303-312.
Guzik K. et al., Small-molecule inhibitors of the programmed cell death-1/programmed death-ligand 1 (PD-1/PD-L1) interaction via transiently induced protein states and dimerization of PD-L1; J.Med. Chem., 2017, 60(13), 5857-5867.
Han Ya et al., PD-1/PD-L1 inhibitor screening of caffeoylquinic acid compounds using surface plasmon resonance spectroscopy; Analytical Biochemistry, 2018, 547, 52-56.
Hodi FS et al, Bevacizumab plus ipilimumab in patients with metastatic melanoma; Cancer Immunol Res, 2014, 2 (7),632-642.
Hughes P.E. et al., Targeted therapy and checkpoint immunotherapy combinations for the treatment of cancer; Trends Immunol., 2016, 37 (7), 462-476.
Iwai et al., Cancer immunotherapies targeting the PD-1 signaling pathway; J. Biomedical Sci., 2017, 24-26, 1-11.
Loree J.M. et al., Recent developments in the treatment of metastatic colorectal cancer; Ther. Adv. Med. Oncol., 2017, 9 (8), 551-564.
Luke J.J. et al., Kinase inhibitors and immune check-point blockade for the treatment of metastatic melanoma and advanced cancer: synergistic or antagonistic?; Expert Opinion on Pharmacotherapy, 2013, 14, (18), 2457-2462.
Majithia N. et al., Regorafenib in the treatment of colorectal cancer; Expert Opinion on Pharmacotherapy, 2016, 17, (1), 137-145.
Maute R.L. et al., Engineering high-affinity PD-1 variants for optimized immunotherapy and immuno-PET imaging; Proc.Natl. Acad.Sci., 2015, 112(47), E6506-14.
Ngiow SF et al, Anti-TIM3 antibody promotes T cell IFN-γ-mediated antitumor immunity and suppresses established tumors; Cancer res., 2011,71(10),3540-3551.
Peng et al., PD-1 Blockade enhances T-cell migration to tumors by elevating IFN-γ inducible chemokines; Cancer Research, 2012, 72(20), 5209-5218.
Ray E.M. et al., Optimal therapy for patients with hepatocellular carcinoma and resistance or intolerance to sorafenib: challenges and solutions; J. Hepatocell Carcinoma, 2017, 4, 131-138.
Rimassa L. et al., Regorafenib for the treatment of unresectable hepatocellular carcinoma; Expert Rev. Anticancer Ther., 2017, 17 (7), 567-576.
Schmieder R. et al, Regorafenib (BAY 73-4506): Antitumor and antimetastatic activities in preclinical models of colorectal cancer; Int J Cancer, 2014,135(6),1487-1496.
Schroeder B. et al.. Targeting gastrointestinal stromal tumors: the role of regorafenib; Onco Targets Ther., 2016, 9, 3009-3016.
Shindo Y. et al., Combination immunotherapy with 4-1BB activation and PD-1 blockade enhances antitumor efficacy in a mouse model of subcutaneous tumor; Anticancer Res., 2015, 35(1), 129-136.
Schultheis : "Regorafenib in combination with FOLFOX or FOLFIRI as firstor second-line treatment of colorectal cancer: results of a multicenter, phase lb study" Ann Oncol, Jun. 2013;24(6):1560-7. doi: 10.1093/annonc/mdt056. Epub Mar. 13, 2013.
Taylor A. et al., Small-molecule inhibition of PD-1 transcription is an effective alternative to antibody blockade in cancer therapy; Cancer Res., 2018, 78(3), 706-717.
Wilhelm SM et al, Regorafenib (BAY 73-4506): a new oral multikinase inhibitor of angiogenic, stromal and oncogenic receptor tyrosine kinases with potent preclinical antitumor activity; Int J Cancer, 2011,129(1),245-255.
Zak K.M. et al., Structural biology of the immune checkpoint receptor PD-1 and its ligands PD-L1/PD-L2; Structure, 2017, 25(8), 1163-1174.
Tsai et al:"A Multikinase and DNA-PK inhibitor . . . " (Cancer Immunology Research, 2017, vol. 5, pp. 790-803) (Year: 2012).
Ravandi et al., "Idarubicin, cytarabine, and nivolumab in patients with newly diagnosed acute myeloid leukaemia or high-risk myelodysplastic syndrome: a single-arm, phase 2 study" Lancet Haematology, Sep. 2019; 6: e480-e488.
Wu et al., Regorafenib promotes anti-tumor immunity via inhibiting PD-L1 and IDO1 expression in melanoma, (2019) American Association for Cancer Research, DOI: 10.1158/1078-0432.CCR-18-2840, downloaded from clincancerres.aacrjournals.org.
Fukuoka et al., Regorafenib Plus Nivolumab in Patients With Advanced Gastric or Colorectal Cancer: An Open-Label, Dose-Escalation, and Dose-Expansion Phase lb Trial (Regonivo, EPOC1603), J Clin Oncol 38. (2020) p. 1-9.
El-Khoueiry et al.. Poster—Phase 1b study of regorafenib plus pembrolizumab for first-line treatment of advanced hepatocellular carcinoma, ASCO-Gastrointestinal Cancers Symposium, Jan. 23-25, 2020, San Francisco.
Hoff et al., Poster-Immunomodulation by regorafenib alone and in combination with anti-PD-1 antibody on murine models of colorectal cancer, The European Society for Medical Oncology, Sep. 8-12, 2017, Madrid, Spain.
Wiesenthal, Human Tumor Assay Journal, on-line at http://weisenthal.org/synergy1.htm, Mar. 14, 2012.
PTO formSB08 from co-pending U.S. Appl. No. 16/731,409 dated Sep. 30, 2020 (1 page).
Le, "PD-1 Blockade in Tumors with Mismatch-Repair Deficiency" NEJM, 372:2509-2520, 2015.

(56) References Cited

OTHER PUBLICATIONS

Reck et al., "Pembrolizumab versus Chemotherapy for PD-L1-Positive Non-Small-Cell Lung Cancer" NEJM, 375:1823-1833, 2016.
Varchetta, "PD-1/PD-L1 expression and regorafenib clinical efficacy on refractory pancreatic cancer patient." J Clin Oncol, 34, Supplement 15, e15684, May 2016.
Form PTO-892 issued May 11, 2021 in corresponding U.S. Appl. No. 16/731,409 (1 page).
Menon S. et al., "Advances in Cancer Immunotherapy in Solid Tumors"; Cancers, 2016, 8, 106, 1-21.
Nishida T. et al., "The standard diagnosis, treatment and followup of gastrointestinal stromal tumors based on guidelines"; Gastric Cancer, 2016, 19 (1), 3-14.
Sweis R.F. et al., "Mechanistic and pharmacologic insights on immune checkpoint inhibitors"; Pharm. Res., 2017, 120, 1-9.
V. G. Belikov. Pharmaceutical chemistry. Moscow, High School, 1993, Tom. 1, p. 43-47 (in Russian) and English translation thereof (pp. 1-7).
Wiesenthal, Human Tumor Assay Journal, downloaded on-line at http://weisenthal.org/synergy1.htm on Mar. 14, 2012 (1 page).
*OSI Pharmaceuticals, LLC*v *Apotex et al.* , Federal Circuit 2018-1925, (Oct. 4, 2019) (pp. 1-20).
Vengerovsky A.I.: "Pharmacological incompatibility", Bulletin of Siberian Medicine, 2003, No. 3, pp. 49-56 (in Russian) and English translation thereof (pp. 1-15).
—D. A. Kharkevich. Pharmacology: Textbook, 2010, 10th edition, Publisher: GEOTAR-Media, p. 73 (in Russian) and English translation thereof (pp. 1-4).

\* cited by examiner

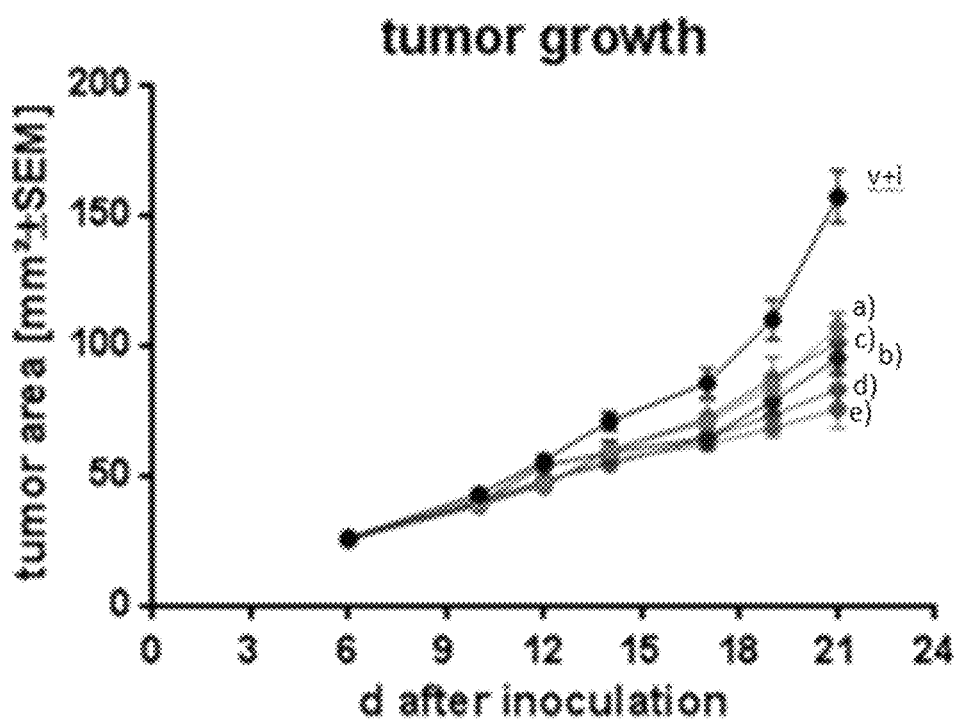

COMBINATION OF REGORAFENIB AND PD-1/PD-L1(2) INHIBITORS FOR TREATING CANCER

The present invention relates to pharmaceutical compositions and combinations comprising regorafenib or its hydrate, solvate, metabolite or pharmaceutically acceptable salt or a polymorph thereof and a PD-1/PD-L1(2) inhibitor for treating, preventing or managing diseases and conditions including hyperproliferative disorders such as cancer in humans and other mammals.

Regorafenib which is 4{4-[3-(4-chloro-3-trifluoromethylphenyl)-ureido]-3-fluorophenoxy}-pyridine-2-carboxylic acid methylamide, a compound of formula (I)

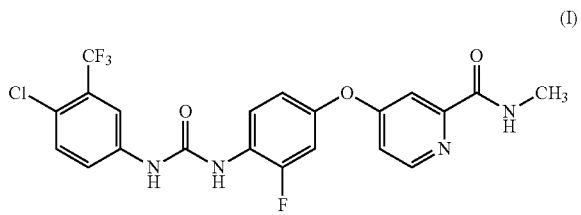 [SMILES: CNC(=O)c1cc(Oc2ccc(NC(=O)Nc3ccc(Cl)c(C(F)(F)F)c3)c(F)c2)ccn1]

is a potent anti-cancer, anti-angiogenic and anti-metastatic agent that possesses various activities including inhibitory activity on the VEGFR, PDGFR, raf, p38, and/or flt-3 kinase signalling molecules and it can be used in treating various diseases and conditions like hyper-proliferative disorders such as cancers, tumors, lymphomas, sarcomas and leukemias as described in WO 2005/009961. It is currently approved for the treatment of colorectal cancer, gastrointestinal stromal tumors and liver cancer under specific conditions. Furthermore salts of the compound of formula (I) such as its hydrochloride, mesylate and phenylsulfonate are mentioned in WO 2005/009961. The monohydrate of the compound of formula (I) is mentioned in WO 2008/043446. An improved process for the manufacturing of regorafenib in high purity is described in WO 2011/128261.

Recently, the PD-1/PD-L1(2) signaling pathway has emerged as important regulator of the activity of the immune system. In cancer, tumor cells express PD-L, the ligand of PD-1, by which they can evade their killing by the host immune system. Inhibitors against PD-1 and its ligands PD-L and PD-L2 have recently been developed which interfere with this immune-suppressive mechanism and have shown amazing clinical efficacy, by extension of the overall survival of patients with various types of cancer. Some of these inhibitors have been approved for various cancer indications such as melanoma, NSCLC, HNSCC, RCC, bladder cancer and NHL. A large number of additional clinical trials are in progress in other indications and/or in combination with a variety of other antitumor agents in order to improve the therapeutic activity (Iwai et al, J. Biomedical Sci. (2017) 24:26, 1-11; Sweis and Luke, Pharm. Res. (2017) 120, 1-9; Bersanelle and Buti, World Journal of Clinical Oncology, (2017) 8(1), 37-53; Park et al., Arch. Pharm. Res. (2016) 39, 1577-1587).

PD-1 inhibitors are biologics, primarily immunoglobulins of the G subclass, which bind to programmed cell death protein 1 also known as PD-1 and block its activity. Know PD-1 inhibitors are nivolumab (Opdivo, BMS-936558, MDX1106), pembrolizumab (Keytruda, MK-3475, lambrolizumab), pidilizumab (CT-011), PDR-001, JS001, STI-A1110, AMP-224 and AMP-514 (MEDI0680). The latter two are PD-L2 fusion proteins. (Iwai et al, J. Biomedical Sci. (2017) 24:26, 1-11; Menon et al., Cancers (2016) 8, 106, 1-21)

PD-1(CD279) is a receptor protein which is expressed as monomer on the surface of various immune cells mainly on activated CD4+ and CD8+ T cells, on macrophages and on activated B cells, but was also found on natural killer (NK) cells and antigen presenting cells (APC). The extracellular domain of this type I membrane protein consists of a single IgV-like domain, followed by a transmembrane domain and a cytoplasmic region, which contains an immunoreceptor tyrosine-based inhibitory and switch motifs (ITIM and ITSM). Upon binding to its ligand PD-L or PD-L2, the phosphatase SHP-2 is recruited which dephosphorylates the kinase ZAP70, a major component of the T cell receptor (TCR) signaling complex. This shuts down TCR signaling and inhibits the cytotoxic activity of the T cells, their interferon γ production and proliferation. In addition, PD-1 ligation up-regulates E3-ubiquitin ligases CBL-b and c-CBL that trigger T cell receptor down-modulation. PD-1 is encoded by the Pdcd1 gene in humans and is transcriptionally activated by transcription factors NFATc1, IRF9 and FoxO1, which are activated upon TCR activation and by T cell exhaustion signals such as transforming growth factor ß and eomesodermin. The activation induced expression of PD-1 suggests that this receptor regulates rather the later phase of the immune response in the peripheral tissue (effector phase, memory response and chronic infection). This is in contrast to CTLA-4, another immune check point protein, which is more active in the earlier priming phase of the immune response and inhibitors of CTLA-4 (e.g. ipilimumab) appear to be less well tolerated in patients. (Iwai et al, J. Biomedical Sci. (2017) 24:26, 1-11; Sweis and Luke, Pharm. Res. (2017) 120, 1-9; Park et al., Arch. Pharm. Res. (2016) 39, 1577-1587).

PD-L inhibitors are biologics, primarily immunoglobulins of the G subclass, which bind to the ligand of PD-1 and block its activity. Know PD-L inhibitors are atezolizumab (Tecentriq, MPDL3280A), durvalumab (MEDI4736), avelumab (MSB0010718C), BMS-936559 (MDX1105) and LY3300054.

PD-L (B7-H1, CD274) is one of the ligands of PD-1. PD-L is broadly expressed on the cell surface of many different immune cell populations (e.g. T-, B- NK-cells, DC, monocytes, macrophages), on activated vascular endothelial cells, but also epithelial cells including tumor cells of various entities such as melanoma, lung, ovarian and colon cancers. The expression of PD-L is enhanced by pro-inflammatory cytokines such as interferon γ, interferon Type I and γ chain cytokines (IL-2, -4, -7, -9, -15, -21). As described above, T cell activation is inhibited upon interaction with PD-1 and thereby the immune response is dampened. (Park et al., Arch. Pharm. Res. (2016) 39, 1577-1587; Menon et al., Cancers (2016) 8, 106, 1-21)

PD-L2 (CD273, B7-DC) is the second ligand identified to bind to PD-1. It is also a membrane bound protein and its expression is restricted to a small subset of immune cells (DC and macrophages) and occurs in a few tumor indications such cancers of the liver, cervix and esophagus. Currently PD-L2 is used as fusion proteins are under development as therapeutic to block the activity of PD-1 and eventually PD-L2 inhibitors may emerge as therapeutic agents as well.

In the first instance PD-1/PD-L1 inhibitors encompass antibody biologics. However, more recent investigations have let to the discovery of other types of inhibitors of PD-1/PD-L1(2), such as small molecules and peptides.

Examples of small molecule inhibitors of PD-1/PD-L1 described are BMS-202, BMS-8, BMS-37 (Zak et al., Structure. 2017 Aug. 1; 25(8):1163-1174; Guzik et al., J Med Chem. 2017 Jul. 13; 60(13):5857-5867), CA-170, CA-137 (Tuck D ICI symposium March 2017) and caffeoylquinic acid compounds (Han et al., Anal Biochem. 2018 Apr. 15; 547:52-56). Examples of peptide inhibitors are described in Maute et al., (Proc Natl Acad Sci USA. 2015 Nov. 24; 112(47):E6506-14). Furthermore small molecule inhibitors which affect the transcription of PD-1 such as the GSKa/ß inhibitor SB415286 have also been identified (Taylor et al., Cancer Res. 2018 Feb. 1; 78(3):706-717).

In WO 2015/11993 combinations of VEGF inhibitors and PD-1 antagonists for the treatment of cancer is described.

Object of the present invention is the improvement of cancer therapy by the administration of regorafenib and a PD-1/PD-L1(2) inhibitor in combination.

Surprisingly the combination of regorafenib and a PD-1/PD-L1(2) inhibitor shows a significant efficacy improvement over the sum of the monotherapies, in particular a significant antitumor and/or antimetastatic efficacy improvement. Furthermore the profile of the side effects (e.g. hand-foot syndrome, elevated blood pressure, fatigue, diarrhea and mucosal inflammation) can be improved.

The present invention pertains to a combination comprising regorafenib which is the compound of the formula (I)

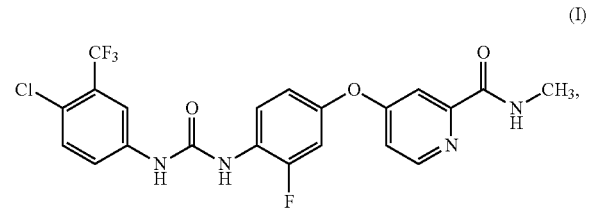 [SMILES: CNC(=O)c1cc(Oc2ccc(NC(=O)Nc3ccc(Cl)c(C(F)(F)F)c3)c(F)c2)ccn1]

(I)

or its hydrate, solvate, metabolite or pharmaceutically acceptable salt of thereof, or a polymorph thereof and a PD-1/PD-L1(2) inhibitor.

The term "the compound of formula (I)" or "regorafenib" refers to 4-{4-[({[4-chloro-3-(trifluoromethyl)phenyl]amino}carbonyl)amino]-3-fluorophenoxy}-N-methylpyridine-2-carboxamide as depicted in formula (I).

Solvates for the purposes of the invention are those forms of the compounds or their salts where solvent molecules form a stoichiometric complex in the solid state and include, but are not limited to for example water, ethanol and methanol.

Hydrates are a specific form of solvates, where the solvent molecule is water. Hydrates of the compounds of the invention or their salts are stoichiometric compositions of the compounds or salts with water, such as, for example, hemi-, mono- or dihydrates. Preference is given to the monohydrate of regorafenib.

Salts for the purposes of the present invention are preferably pharmaceutically acceptable salts of the compounds according to the invention. Suitable pharmaceutically acceptable salts are well known to those skilled in the art and include salts of inorganic and organic acids, such as hydrochloric acid, hydrobromic acid, sulfuric acid, phosphoric acid, methanesulphonic acid, trifluoromethanesulfonic acid, benzenesulfonic acid, p-toluenesulfonic acid (tosylate salt), 1-naphthalenesulfonic acid, 2-naphthalenesulfonic acid, acetic acid, trifluoroacetic acid, malic acid, tartaric acid, citric acid, lactic acid, oxalic acid, succinic acid, fumaric acid, maleic acid, benzoic acid, salicylic acid, phenylacetic acid, and mandelic acid. In addition, pharmaceutically acceptable salts include salts of inorganic bases, such as salts containing alkaline cations (e.g., $Li^+$ $Na^+$ or $K^+$), alkaline earth cations (e.g., $Mg^{+2}$, $Ca^{+2}$ or $Ba^{+2}$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, lysine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU). Preference is given to the hydrochloride, mesylate or phenylsulfonate salt of regorafenib.

Metabolites of regorafenib for the purpose of the present invention include 4-[4-({[4-chloro-3-(trifluoromethyl)phenyl]carbamoyl}amino)-3-fluorophenoxy]-N-methylpyridine-2-carboxamide 1-oxide, 4-[4-(([4-chloro-3-(trifluoromethyl)phenyl]carbamoyl amino)-3-fluorophenoxy]-N-(hydroxymethyl)pyridine-2-carboxamide, 4-[4-(([4-chloro-3-(trifluoromethyl)phenyl]carbamoyl)amino)-3-fluorophenoxy]pyridine-2-carboxamide and 4-[4-(([4-chloro-3-(trifluoromethyl)phenyl]carbamoyl amino)-3-fluorophenoxy]pyridine-2-carboxamide 1-oxide. Preferred are regorafenib and the monohydrate of regorafenib as a compound of the present invention.

The compounds of the invention may be prepared by use of known chemical reactions and procedures.

The term "PD-1/PD-L1(2) inhibitor" refers to an anti-PD-1 antibody including but not limited to nivolumab (Opdivo, BMS-936558, MDX1106), pembrolizumab (Keytruda, MK-3475, lambrolizumab), pidilizumab (CT-011), PDR-001, JS001, STI-A1110, AMP-224 and AMP-514 (MEDI0680), or refers to an anti-PD-L1 antibody including but not limited to atezolizumab (Tecentriq, MPDL3280A), durvalumab (MEDI4736), avelumab (MSB0010718C), BMS-936559 (MDX1105) and LY3300054 or refers to an anti-PD-L2 antibody.

Preference is given to nivolumab or pembrolizumab or pidilizumab as anti-PD-1 antibody.

Furthermore atezolizumab or durvalumab or avelumab are preferred as anti-PD-L1 antibody.

The term "PD-1/PD-L1(2) inhibitor" also refers to small molecules and peptides including but not limited to BMS-202, BMS-8, BMS-37, caffeoylquinic acid compounds and the GSKa/ß inhibitor SB415286.

Method for Treatment:

The present invention also relates to a method for using the combination and compositions thereof, to treat mammalian hyper-proliferative disorders. This method comprises administering to a mammal in need thereof, including a human, an amount of the combination, which is effective to treat the disorder. Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small intestine, and salivary gland cancers.

Preference is given to colorectal cancer.

Preference is also given to gastrointestinal stromal tumors (GIST).

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Preference is given to hepatic cell cancer.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention. Based upon standard laboratory techniques known to evaluate compounds useful for the treatment of hyper-proliferative disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The present invention further provides the use of the compound of the invention for the preparation of a pharmaceutical compositions for the treatment of the aforesaid disorders.

Administration

Combinations of the present invention can be administered in any form by any effective route, including, e.g., oral, parenteral, enteral, intravenous, intraperitoneal, topical, transdermal (e.g., using any standard patch), ophthalmic, nasally, local, non-oral, such as aerosol, inhalation, subcutaneous, intramuscular, buccal, sublingual, rectal, vaginal, intra-arterial, and intrathecal, etc. They can be administered alone, or in combination with any ingredient(s), active or inactive.

Preference is given to an oral administration of regorafenib e.g. as tablet.

Preferably the PD-1/PD-L1(2) inhibitor can be administered intravenously.

Combinations of the present invention can be converted in a known manner into the usual formulations, which may be liquid or solid formulations e.g. without limitation normal and enteric coated tablets, capsules, pills, powders, granules, elixirs, tinctures, solution, suspensions, syrups, solid and liquid aerosols and emulsions.

Generally, the use of the combinations of the present invention mentioned before will serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce inhibitoric effects.

"Combination" means for the purposes of the invention not only a dosage form which contains all the components (so-called fixed combinations), and combination packs containing the components separate from one another, but also components which are administered simultaneously or sequentially, as long as they are employed for the prophylaxis or treatment of the same disease.

The amount of the administered active ingredient can vary widely according to such considerations as the particular compound and dosage unit employed, the mode and time of administration, the period of treatment, the age, sex, and general condition of the patient treated, the nature and extent of the condition treated, the rate of drug metabolism and excretion, the potential drug combinations and drug-drug interactions, and the like.

An aspect of the invention of particular interest is a combination comprising the administration of regorafenib in an amount of 4 to 400 mg, preferably from 10 to 200 mg, more preferably from 10 to 100 mg and the administration of the PD-1/PD-L1(2) inhibitor in an amount of 0.005 to 10 mg/kg, preferably from 1 to 10 mg/kg by weight of patient.

According to the present invention regorafenib and the PD-1/PD-L1(2) inhibitor can be administered concomitantly.

In a further aspect of the present invention regorafenib is administered first followed by the administration of the PD-1/PD-L1(2) inhibitor.

Alternatively the PD-1/PD-L1(2) inhibitor is administered first followed by the administration of regorafenib which is the preferred way of administration.

The pharmaceutical composition according to the invention is administered one or more, preferably up to three, more preferably up to two times per day. Preference is given to an administration of regorafenib via the oral route and of the PD-1/PD-L1(2) inhibitor via the intravenous route.

Nevertheless, it may in some cases be advantageous to deviate from the amounts specified, depending on body weight, individual behaviour toward the active ingredient, type of preparation and time or interval over which the administration is affected. For instance, less than the aforementioned minimum amounts may be sufficient in some cases, while the upper limit specified has to be exceeded in other cases. In the case of administration of relatively large amounts, it may be advisable to divide these into several individual doses over the day.

The combination can comprise effective amounts of the compound of Formula I and the PD-1/PD-L1(2) inhibitor, which achieves a greater therapeutic efficacy than when either compound is used alone.

The relative ratios of each compound in the combination can also be selected based on their respective mechanisms of action and the disease biology. The relative ratios of each compound can vary widely.

The release of one or more agents of the combination can also be controlled, where appropriate, to provide the desired therapeutic activity when in a single dosage form, combination pack, kit or when in separate independent dosage forms.

The present invention includes pharmaceutical compositions which are comprised of a pharmaceutically acceptable carrier and a pharmaceutically effective amount of the compounds of the present invention. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated.

For oral administration, the compounds can be formulated into solid or liquid preparations such as solid dispersion, capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, *arachis* oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or intraperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A compositions of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material is, for example, cocoa butter and polyethylene glycol.

Controlled release formulations for parenteral administration include liposomal, polymeric microsphere and polymeric gel formulations which are known in the art.

The pharmaceutical compositions of this invention may also be in the form of a solid dispersion. The solid dispersion may be a solid solution, glass solution, glass suspension, amorphous precipitation in a crystalline carrier, eutectic or monotecic, compound or complex formation and combinations thereof.

An aspect of the invention of particular interest is a pharmaceutical composition comprising a solid dispersion, wherein the matrix comprises a pharmaceutically acceptable polymer, such as polyvinylpyrrolidone, vinylpyrrolidone/vinylacetate copolymer, polyalkylene glycol (i.e. polyethylene glycol), hydroxyalkyl cellulose (i.e. hydroxypropyl cellulose), hydroxyalkyl methyl cellulose (i.e. hydroxypropyl methyl cellulose), carboxymethyl cellulose, sodium carboxymethyl cellulose, ethyl cellulose, polymethacrylates, polyvinyl alcohol, polyvinyl acetate, vinyl alcohol/vinyl acetate copolymer, polyglycolized glycerides, xanthan gum, carrageenan, chitosan, chitin, poyldextrin, dextrin, starch and proteins.

Another aspect of the invention is a pharmaceutical composition comprising a solid dispersion, wherein the matrix comprises a sugar and/or sugar alcohol and/or cyclodextrin, for example sucrose, lactose, fructose, maltose, raffinose, sorbitol, lactitol, mannitol, maltitol, erythritol, inositol, trehalose, isomalt, inulin, maltodextrin, β-cyclodextrin, hydroxypropyl-β-cyclodextrin or sulfobutyl ether cyclodextrin.

Additional suitable carriers that are useful in the formation of the matrix of the solid dispersion include, but are not limited to alcohols, organic acids, organic bases, amino acids, phospholipids, waxes, salts, fatty acid esters, polyoxyethylene sorbitan fatty acid esters, and urea.

The solid dispersion of regorafenib in the matrix may contain certain additional pharmaceutical acceptable ingredients, such as surfactants, fillers, disintegrants, recrystallization inhibitors, plasticizers, defoamers, antioxidants, detackifier, pH-modifiers, glidants and lubricants.

The solid dispersion of the invention is prepared according to methods known to the art for the manufacture of solid dispersions, such as fusion/melt technology, hot melt extrusion, solvent evaporation (i.e. freeze drying, spray drying or layering of powders of granules), coprecipitation, supercritical fluid technology and electrostatic spinning method.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to *arachis* oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan monopalmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnauba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithin, sorbitol monooleate, polyoxyethylene sorbitol monooleate, and polyoxyethylene stearate).

It is believed that one skilled in the art, utilizing the preceding information, can utilize the present invention to its fullest extent.

EXAMPLES

Example 1

The combinatorial activity of regorafenib and anti-mouse PD-1 antibody (RMP1-14, Peng et al., Cancer Res., (2012) 72(20), 5209-5218) was investigated in a syngenic murine MC38 CRC model Methods:

MC38 syngeneic tumors were grown subcutaneously in mice and treated with regorafenib and/or anti-mouse PD-1 antibody (RMP1-14) according to the following regimens:

a) regorafenib alone at a dose of 3 mg/kg per day once daily for 15 days as a PluronicF68/PEG400/Propylenglycol (15/42,5/42,5+20% aqua) po (per oral) formulation and 10 mg/kg of a non-binding rIgG2a isotype control (clone 2A3), given every third day for five times in PBS (phosphate buffer saline) as ip (intraperitoneal) formulation, b) anti-mouse PD-1 antibody (RMP1-14) alone dosed at 10 mg/kg every third day for five times as a PBS ip formulation and PluronicF68/PEG400/Propylenglycol (15/42,5/42,5+20% aqua) vehicle once daily for 15 days as po formulation, c) concomitantly, regorafenib at a dose of 3 mg/kg per day once daily for 4 days as a PluronicF68/PEG400/Propylenglycol (15/42,5/42,5+20% aqua) po formulation and anti-mouse PD-1 antibody (RMP1-14) dosed at 10 mg/kg every third day for five times as a PBS ip formulation, d) sequentially, first regorafenib at a dose of 3 mg/kg per day once daily for 4 days as a PluronicF68/PEG400/Propylenglycol (15/42,5/42,5+20% aqua) po formulation, followed on day 5 post randomization by anti-mouse PD-1 antibody (RMP1-14) dosed at 10 mg/kg every third day for four times as a PBS ip formulation, e) sequentially, first anti-mouse PD-1 antibody (RMP1-14) dosed at 10 mg/kg every third day twice as a PBS ip formulation, followed on day 5 post randomization by regorafenib at a dose of 3 mg/kg per day once daily for 10 days as a PluronicF68/PEG400/Propylenglycol (15/42,5/42, 5) po formulation.

Control animals were treated concomitantly with the regorafenib vehicle (PluronicF68/PEG400/Propylenglycol (15/42,5/42,5+20% aqua)) and a non-binding isotype control antibody (rat IgG2a, clone 2A3). Tumor growth was monitored by caliper measurement and the tumor area was calculated using the formula a×b where a and b are the long and short diameters of the tumor, respectively. Tumor weights were measured after completion of the study. Tumor vs control (T/C) was calculated using vehicle treated animals as reference.

Results:

Both regorafenib and anti-mouse PD-1 antibody inhibited the growth of MC38 tumors vs control, and this effect was significantly enhanced by concomitant treatment or when regorafenib was given after anti PD1.

TABLE 1

| Treatment | T/C (area) | T/C (weight) |
|---|---|---|
| Vehicle/Iso | 1.00 | 1.00 |
| Regorafenib (3 mg/kg) according to regimen a) | 0.68 | 0.64 |
| PD-1 (10 mg/kg) according to regimen b) | 0.61 | 0.56 |
| First Regorafenib (3 mg/kg), followed by PD-1 (10 mg/kg) according to regimen d) | 0.64 | 0.71 |
| Regorafenib (3 mg/kg) and PD-1 (10 mg/kg) concomitantly according to regimen c) | 0.53 | 0.39 |
| First PD-1 (10 mg/kg), followed by Regorafenib (3 mg/kg) according to regimen e) | 0.48 | 0.41 |

FIG. 1: Antitumor activity of Regorafenib and anti PD-1 alone and in combination in a syngenic murine MC38 CRC model: v+i=vehicle+isotype, a)=regimen a), b)=regimen b), c)=regimen c), d)=regimen d), e)=regimen e)

Example 2

The combinatorial activity of regorafenib and anti-mouse PD-1 antibody (RMP1-14, Peng et al., Cancer Res., (2012) 72(20), 5209-5218) was investigated in a syngenic murine CT26 CRC model CT26 syngeneic tumors were grown orthotopically in mice (Abou-Elkacem et al., Mol Cancer Ther. 2013 July; 12(7):1322-31) and treated with regorafenib and/or anti-mouse PD-1 antibody (RMP1-14) according to the following regimens:

a) regorafenib alone at a dose of 30 mg/kg per day once daily for 10 days as a PluronicF68/PEG400/Propylenglycol/water (12/34/34/20) po (per oral) formulation using the formulation vehicle alone as control or in a combination with an unspecific control antibody given intraperitoneally (i.p.) at a dose of 20 mg/kg in PBS every third day.

b) anti-mouse PD-1 antibody (RMP1-14) alone dosed at 20 mg/kg every third day for four times as a PBS i.p. formulation and an unspecific antibody was used as control c) in combination, regorafenib at a dose of 20 mg/kg per day once daily for 10 days as a PluronicF68/PEG400/Propylenglycol/water (/12/34/34/20) p.o. formulation and anti-mouse PD-1 antibody (RMP1-14) dosed at 20 mg/kg every third day for four times as a PBS i.p. formulation, After the treatment was stopped some mice were observed for a period of another 11 days in order to investigate the regrowth of the tumor (data not shown) and the appearance of liver metastases (table 2). Mice were sacrificed at the end of treatment or at the end of the observation period and livers were screened macroscopically for metastases on their surface. The number of mice with liver metastases was then related to the total number of mice in the respective study arm.

TABLE 2

The combination of regorafenib and anti-PD1 prevents liver metastasis more efficiently in comparison to the single agents

| time of analysis p.i. | prior treatment d 4 | after treatment for 14 days d 14 | | | observation period after treatment stop at d 14 d 25 | | |
|---|---|---|---|---|---|---|---|
| vehicle | − | + | − | − | − | − | − |
| control antibody | − | − | − | + | − | + | − |
| regorafenib | − | − | + | − | − | + | + |
| anti PD1 | − | − | − | − | + | − | + |
| total # of animals | 6 | 6 | 6 | 5 | 6 | 8 | 7 |
| # of animals with mets | 0 | 4 | 0 | 3 | 4 | 8 | 0 |
| % animals wirth mets | 0 | 67 | 0 | 60 | 67 | 100 | 0 | d: day;
p.i.: post injection

In table 2 it is indicated with a "+" which test system was used. After 14 days treatment with regorafenib 0 of 6 animals and in the PD-1 group 4 of 6 animals showed metastases. Whereas after 25 days treatment the combination of regorafenib and control antibody showed in 8 of 8 animals metastases but the in the group treated with the combination of regorafenib and PD-1 surprisingly no animal showed metastases.

BRIEF DESCRIPTION OF THE DRAWING

FIG. 1 illustrates a graph of the antitumor activity of Regorafenib and anti PD-1 alone and in combination in a syngenic murine MC38 CRC model: v+i=vehicle+isotype, a)=regimen a), b)=regimen b), c)=regimen c), d)=regimen d), e)=regimen e).

What is claimed is:

1. A pharmaceutical combination comprising chemotherapeutic agents, wherein said chemotherapeutic agents consist of
   1) regorafenib or its hydrate, solvate, metabolite or pharmaceutically acceptable salt, or a polymorph thereof and
   2) nivolumab,
   wherein the regorafenib metabolite is selected from the group consisting of:
   4-[4-({[4-chloro-3-(trifluoromethyl)phenyl]carbamoyl}amino)-3-fluorophenoxy]-N-methylpyridine-2-carboxamide I-oxide,
   4-[4-({[4-chloro-3-(trifluoromethyl)phenyl]carbamoyl}amino)-3-fluorophenoxy]-N-(hydroxymethyl)pyridine-2-carboxamide,
   4-[4-({[4-chloro-3-(trifluoromethyl)phenyl]carbamoyl}amino)-3-fluorophenoxy]pyridine-2-carboxamide and
   4-[4-({[4-chloro-3(trifluoromethyl)phenyl]carbamoyl}amino)-3-fluorophenoxy]pyridine-2-carboxamide I-oxide and
   wherein said chemotherapeutic agents are separate from one another.

2. The combination of claim 1 which is a combination pack.

3. The combination of claim 1 wherein said chemotherapeutic agents are in separate dosage forms for administration simultaneously or sequentially for use in the treatment of the same disease in a subject.

4. The combination of claim 3 for sequential administration wherein a regorafenib dosage form is for administration first followed by the administration of a nivolumab dosage form.

5. The combination of claim 1 wherein regorafenib is in an oral dosage form and nivolumab is in an intravenous dosage form.

6. The combination of claim 1 wherein regorafenib is in a dosage form in an amount of 10 to 100 mg.

7. The combination of claim 1 with combined dosages for treating malignant disorders and pre-malignant hyper-proliferative disorders.

8. The combination of claim 1 with combined dosages for treating hyper-proliferative disorders wherein the hyper-proliferative disorders are selected from the group consisting of cancers of the breast, respiratory tract, brain, reproductive organs, digestive tract, urinary tract, eye, liver, skin, head and neck, thyroid, parathyroid and their distant metastases.

9. The combination of claim 8 wherein the hyper-proliferative disorders are selected from the group consisting of hepatic cell cancer, colorectal cancer and gastrointestinal stromal tumors (GIST).

10. The combination of claim 8 wherein the hyper-proliferative disorder is hepatic cell cancer.

11. The combination of claim 8 wherein the hyper-proliferative disorder is colorectal cancer.

12. A method of treating malignant disorders and pre-malignant hyper-proliferative disorders in a subject in need thereof comprising administering chemotherapeutic agents, wherein said chemotherapeutic agents are separate from one another and consist of effective amounts of
   1) regorafenib or its hydrate, solvate, metabolite or pharmaceutically acceptable salt, or a polymorph thereof and
   2) nivolumab,
   wherein the regorafenib metabolite is selected from the group consisting of:
   4-[4-({[4-chloro-3-(trifluoromethyl)phenyl]carbamoyl}amino)-3-fluorophenoxy]-N-methylpyridine-2-carboxamide I-oxide,
   4-[4-({[4-chloro-3-(trifluoromethyl)phenyl]carbamoyl}amino)-3-fluorophenoxy]-N-(hydroxymethyl)pyridine-2-carboxamide,
   4-[4-({[4-chloro-3-(trifluoromethyl)phenyl]carbamoyl}amino)-3-fluorophenoxy]1pyridine-2-carboxamide and
   4-[4-({[4-chloro-3(trifluoromethyl)phenyl]carbamoyl}amino)-3-fluorophenoxy]1pyridine-2-carboxamide I-oxide.

13. The method of claim 12 wherein regorafenib is administered first followed by the administration of nivolumab.

14. The method of claim 12 wherein regorafenib is administered orally and nivolumab is administered intravenously.

15. The method of claim 12 wherein regorafenib is administered in the form of a tablet and nivolumab is administered intravenously.

16. A method of treating hyper-proliferative disorders in a subject in need thereof comprising administering chemotherapeutic agents, wherein said chemotherapeutic agents are separate from one another and consist of effective amounts of
1) regorafenib or its hydrate, solvate, metabolite or pharmaceutically acceptable salt, or a polymorph thereof and
2) nivolumab,
wherein the hyper-proliferative disorders are selected from the group consisting of cancers of the breast, respiratory tract, brain, reproductive organs, digestive tract, urinary tract, eye, liver, skin, head and neck, thyroid, parathyroid and their distant metastases.

17. The method of claim 16 wherein said chemotherapeutic agents consist of effective amounts of
1) regorafenib and
2) nivolumab,
wherein the hyper-proliferative disorders are selected from the group consisting of hepatic cell cancer, colorectal cancer and gastrointestinal stromal tumors (GIST).

18. The method of claim 17 wherein regorafenib is administered in the form of a tablet and nivolumab is administered intravenously.

19. The method of claim 16 wherein the hyper-proliferative disorder is hepatic cell cancer.

20. The method of claim 16 wherein the hyper-proliferative disorder is colorectal cancer.

21. The method of claim 16 wherein regorafenib is administered first followed by the administration of nivolumab.

22. The method of claim 16 wherein regorafenib is administered orally and nivolumab is administered intravenously.

23. A pharmaceutical combination comprising separate chemotherapeutic agents, wherein said chemotherapeutic agents consist of
1) regorafenib and
2) nivolumab.

24. The combination of claim 23 wherein regorafenib is in the form of a tablet in an amount of 10 to 100 mg and nivolumab is in an intravenous dosage form.

* * * * *